(12) United States Patent
Jang et al.

(10) Patent No.: US 11,540,721 B2
(45) Date of Patent: Jan. 3, 2023

(54) ANTIOXIDANT SENSOR AND METHOD OF MEASURING ANTIOXIDANT VALUE

(71) Applicant: SAMSUNG ELECTRONICS CO., LTD., Suwon-si (KR)

(72) Inventors: Hyeong Seok Jang, Seoul (KR); Kun Sun Eom, Yongin-si (KR); Jin Young Park, Hwaseong-si (KR); Sung Mo Ahn, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 374 days.

(21) Appl. No.: 16/843,479

(22) Filed: Apr. 8, 2020

(65) Prior Publication Data

US 2021/0113087 A1 Apr. 22, 2021

(30) Foreign Application Priority Data

Oct. 22, 2019 (KR) .................. 10-2019-0131279

(51) Int. Cl.
*A61B 5/00* (2006.01)
*G01N 21/63* (2006.01)

(52) U.S. Cl.
CPC .......... *A61B 5/0075* (2013.01); *A61B 5/0053* (2013.01); *A61B 5/443* (2013.01); *G01N 21/63* (2013.01)

(58) Field of Classification Search
CPC .. G01N 21/474; G01N 21/3151; G01N 21/63; G01N 2021/3181; G01N 2021/4759; G01N 2021/3148; A61B 5/6843; A61B 5/443; A61B 5/0075; A61B 5/0053; A61B 5/486
See application file for complete search history.

(56) References Cited

U.S. PATENT DOCUMENTS

| | | | |
|---|---|---|---|
| 6,205,354 B1 | 3/2001 | Gellermann et al. | |
| 7,248,911 B2 | 7/2007 | Jeon et al. | |
| 7,734,321 B2 | 6/2010 | White | |
| 8,260,402 B2 | 9/2012 | Ermakov et al. | |
| 10,044,296 B2 | 8/2018 | Vandenbaviere et al. | |
| 10,335,087 B2 | 7/2019 | Lee et al. | |
| 2005/0171413 A1* | 8/2005 | Blair ................ | A61B 5/1455 600/310 |
| 2012/0330164 A1 | 12/2012 | Ermakov et al. | |

(Continued)

FOREIGN PATENT DOCUMENTS

| | | |
|---|---|---|
| KR | 10-2004-0082554 A | 9/2004 |
| KR | 10-2010-0008074 A | 1/2010 |

(Continued)

*Primary Examiner* — Sang H Nguyen
(74) *Attorney, Agent, or Firm* — Sughrue Mion, PLLC

(57) ABSTRACT

An antioxidant sensor includes a pressure sensor configured to obtain a contact pressure between an object and an optical sensor; the optical sensor configured to, based on the obtained contact pressure exceeding a set threshold pressure, emit a first light of a first wavelength to the object, and receive the first light reflected or scattered from the object; and a processor configured to determine a contact portion of the object in contact with the optical sensor, set a threshold pressure, among different threshold pressures, according to the determined contact portion, and determine an antioxidant value based on the received first light.

22 Claims, 11 Drawing Sheets

(56) References Cited

U.S. PATENT DOCUMENTS

| | | | |
|---|---|---|---|
| 2013/0178750 A1* | 7/2013 | Sheehan | A61B 5/0215 |
| | | | 604/9 |
| 2014/0200419 A1* | 7/2014 | Ermakov | A61B 5/4504 |
| | | | 600/476 |
| 2016/0278645 A1 | 9/2016 | Yoon | |
| 2017/0108433 A1* | 4/2017 | Helfmann | G01J 3/0294 |
| 2017/0143210 A1* | 5/2017 | Ikebe | A61B 5/02416 |
| 2018/0014758 A1* | 1/2018 | Yamada | A61B 5/0261 |
| 2019/0130156 A1* | 5/2019 | Yun | A61B 5/0059 |
| 2019/0150746 A1 | 5/2019 | Kim | |

FOREIGN PATENT DOCUMENTS

| | | |
|---|---|---|
| KR | 10-2016-0025286 A | 3/2016 |
| KR | 10-2016-0115017 A | 10/2016 |
| KR | 10-2019-0056871 A | 5/2019 |
| RU | 2014 112 333 A | 10/2015 |
| WO | 2013/023637 A2 | 2/2013 |

* cited by examiner

ANTIOXIDANT SENSOR AND METHOD OF MEASURING ANTIOXIDANT VALUE

CROSS-REFERENCE TO RELATED APPLICATION(S)

This application claims priority from Korean Patent Application No. 10-2019-0131279, filed on Oct. 22, 2019, in the Korean Intellectual Property Office, the entire disclosure of which is incorporated herein by reference for all purposes.

BACKGROUND

1. Field

Example embodiments of the disclosure relate to an apparatus and a method for non-invasively measuring an antioxidant value.

2. Description of the Related Art

Reactive oxygen species act as an important biological defense factor such as white blood cells that protect a body against infections. However, it has been known that excessive generation of reactive oxygen species in the body may lead to various tissue diseases.

Common factors that cause the reactive oxygen species include stress, alcohol, peroxides, medicine, and the like. The reactive oxygen species produced by these factors may cause cranial nerve diseases, circulatory diseases, cancer, digestive tract diseases, liver diseases, arteriosclerosis, renal diseases, diabetes, aging, and the like.

Our bodies have a series of antioxidant defense systems to protect against oxygen toxicity. For normal operation of the systems, it is essential to consume a sufficient amount of antioxidants such as vitamin E, vitamin C, carotenoid, flavonoid, and the like, and it is important to eat as many foods that are rich in antioxidants as possible for an effective antioxidant action. Accordingly, there is a need for an apparatus for easily identifying the amount of antioxidants in the body.

SUMMARY

One or more example embodiments provide an antioxidant sensor and a method of measuring an antioxidant value.

According to an aspect of an example embodiment, there is provided an antioxidant sensor, including: a pressure sensor configured to obtain a contact pressure between an object and an optical sensor; the optical sensor configured to, based on the obtained contact pressure exceeding a set threshold pressure, emit a first light of a first wavelength to the object, and receive the first light reflected or scattered from the object; and a processor configured to determine a contact portion of the object in contact with the optical sensor, set a threshold pressure, among different threshold pressures, according to the determined contact portion, and determine an antioxidant value based on the received first light.

The processor may be further configured to control operation to guide a user such that the contact pressure between the object and the optical sensor exceeds the set threshold pressure.

The processor may be further configured to, based on the obtained contact pressure being less than or equal to the set threshold pressure, adjust at least one of a quantity of light and a flickering speed of the optical sensor.

The processor may be further configured to, based on the obtained contact pressure being less than or equal to the set threshold pressure, to output information indicating that the contact pressure between the object and the optical sensor is to be increased.

The first wavelength may be included in an absorption band of an antioxidant substance.

The first wavelength may be a blue wavelength.

The processor may be further configured to control to inquire a user about the contact portion of the object and determine the contact portion of the object based on a response from the user.

The optical sensor may be further configured to emit a second light of a second wavelength and a third light of a third wavelength to the object, and receive the second light and the third light reflected or scattered from the object; and the processor may be further configured to obtain a hemoglobin index based on the received second light and the received third light, and determine the contact portion of the object based on the obtained hemoglobin index.

The second wavelength may be included in an absorption band of hemoglobin; and the third wavelength may be different from the second wavelength.

The second wavelength may include a green wavelength; and the third wavelength may include a blue wavelength, the green wavelength, or a red wavelength.

The processor may be further configured to obtain a hemoglobin signal based on the received second light, obtain a preprocessing signal based on the received third light, normalize the obtained hemoglobin signal by using the preprocessing signal, and obtain the normalized hemoglobin signal as the hemoglobin index.

The processor may be further configured to determine the contact portion of the object based on a value of the hemoglobin index.

According to an aspect of an example embodiment, there is provided a method of obtaining an antioxidant value, the method including: determining a contact portion of an object in contact with an optical sensor; setting a threshold pressure, among different threshold pressures, according to the determined contact portion; obtaining a contact pressure between the object and the optical sensor; based on the obtained contact pressure exceeding the set threshold pressure, emitting a first light of a first wavelength to the object, and receiving the first light reflected or scattered from the object; and determining an antioxidant value based on the received first light.

The method may further include controlling to guide a user such that the contact pressure between the object and the optical sensor exceeds the set threshold pressure.

The controlling may include, based on the obtained contact pressure being less than or equal to the set threshold pressure, adjusting at least one of a quantity of light and a flickering speed of the optical sensor.

The controlling may include, based on the obtained contact pressure being less than or equal to the set threshold pressure, outputting information indicating that the contact pressure between the object and the optical sensor is to be increased.

The first wavelength may include a blue wavelength included in an absorption band of an antioxidant substance.

The determining the contact portion may include inquiring a user about the contact portion of the object; and determining the contact portion of the object based on a response from the user.

The determining the contact portion may include: emitting a second light of a second wavelength and a third light of a third wavelength to the object, and receiving the second light and the third light reflected or scattered from the object; obtaining a hemoglobin index based on the received second light and the received third light; and determining the contact portion of the object based on the obtained hemoglobin index.

The second wavelength may include a green wavelength included in an absorption band of hemoglobin; and the third wavelength may include a blue wavelength, the green wavelength, or a red wavelength which is different from the second wavelength.

The obtaining the hemoglobin index may include obtaining a hemoglobin signal based on the received second light; obtaining a preprocessing signal based on the received third light; normalizing the obtained hemoglobin signal by using the preprocessing signal; and obtaining the normalized hemoglobin signal as the hemoglobin index.

The determining the contact portion may include determining the contact portion of the object based on a value of the hemoglobin index.

BRIEF DESCRIPTION OF THE DRAWINGS

The above and other aspects and features of the disclosure will become more apparent by describing in detail example embodiments thereof with reference to the attached drawings, in which.

DETAILED DESCRIPTION

Figure 1:
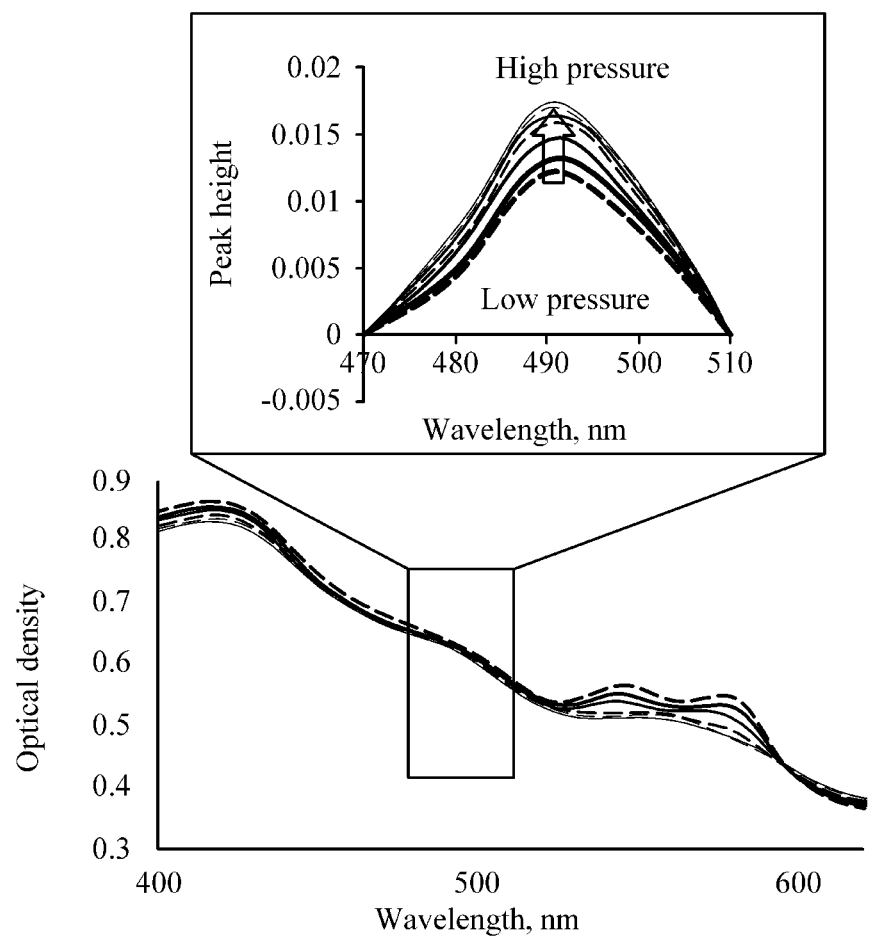
FIG. 1 is a diagram illustrating a change in an optical density spectrum of skin according to pressure applied to skin.

Hereinafter, example embodiments of the disclosure will be described in detail with reference to the accompanying drawings. It should be noted that, in the drawings, the same reference symbols refer to the same parts although illustrated in other drawings. In the following description, a detailed description of known functions and configurations incorporated herein will be omitted when it may obscure the subject matter of the disclosure. Throughout the drawings and the detailed description, unless otherwise described, the same drawing reference numerals will be understood to refer to the same elements, features, and structures. The relative size and depiction of these elements may be exaggerated for clarity, illustration, and convenience.

Process steps described herein may be performed differently from a specified order, unless a specified order is clearly stated as being necessary in the context of the disclosure. That is, each step may be performed in a specified order, at substantially the same time, or in a reverse order, or in any order different from the specified order.

Further, the terms used throughout this specification are defined in consideration of the functions according to example embodiments, and may be varied according to a purpose, an application of the functions and the like of the disclosure. Therefore, definitions of the terms should be understood based on the overall context of the disclosure.

It will be understood that, although the terms first, second, etc. may be used herein to describe various elements, these elements should not be limited by these terms. These terms are only used to distinguish one element from another. Any references to a singular element may include plural elements unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

As used herein, the term "and/or" includes any and all combinations of one or more of the associated listed items. Expressions such as "at least one of," when preceding a list of elements, modify the entire list of elements and do not modify the individual elements of the list. For example, the term "at least one of A and B" or "at least one of A or B" may be used to describe that three cases may exist: only A exists, both A and B exist, and only B exists.

Further, components that will be described in the specification are discriminated merely according to functions mainly performed by the components. That is, two or more components which will be described later may be integrated into a single component. Furthermore, a single component which will be explained later may be separated into two or more components. Moreover, each component may additionally perform some or all of a function executed by another component in addition to the main function thereof. Some or all of the main function of each component may be carried out by another component. Each component may be implemented as hardware, software, or a combination of both.

Figure 2:
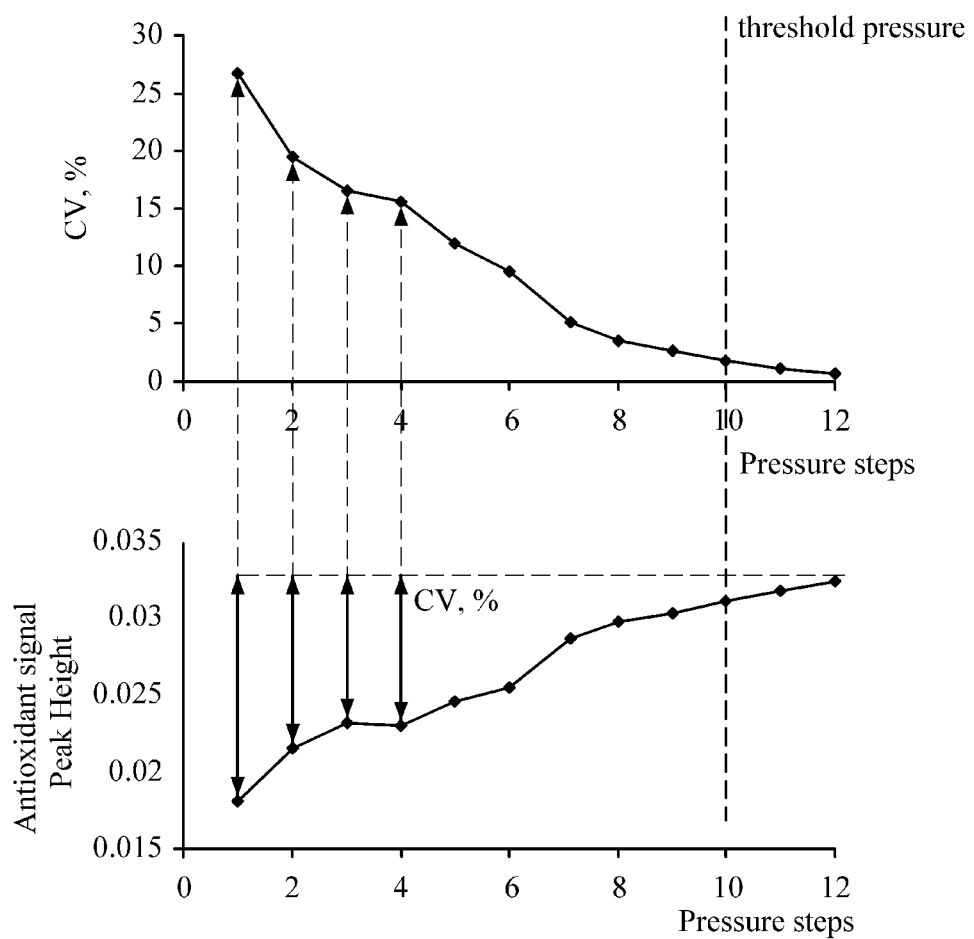
FIG. 2 is a diagram illustrating a change in an antioxidant signal according to pressure applied to skin.

FIG. 1 is a diagram illustrating a change in an optical density spectrum of skin according to pressure applied to skin, and FIG. 2 is a diagram illustrating a change in an antioxidant signal according to pressure applied to skin.

Referring to FIG. 1, it can be seen that an optical density spectrum of skin is changed according to pressure applied to skin. For example, it can be seen from the example of FIG. 1 that in a wavelength band of 470 nm to 510 nm, a peak height of the optical density spectrum of skin increases as pressure applied to skin increases. Here, the wavelength band of 470 nm to 510 nm may be included in a wavelength band, in which an antioxidant signal is measured, e.g., an absorption band of an antioxidant substance (e.g., carotenoid). Further, the peak height may indicate optical density, from which interference caused by a substance other than an antioxidant substance is eliminated by preprocessing (e.g., baseline correction, normalization, etc.).

Referring to FIG. 2, it can be seen that as pressure applied to skin increases, a peak height of an antioxidant signal increases, and at a pressure greater than or equal to a predetermined level, an antioxidant signal is saturated and stabilized. Further, it can be seen that a coefficient of variation (CV) of the peak height of the antioxidant signal decreases as pressure applied to skin increases. Accordingly, by guiding a user to apply pressure, which is greater than or equal to a threshold pressure, to an object, it is possible to measure an antioxidant signal having a high signal-to-noise ratio.

Figure 3:
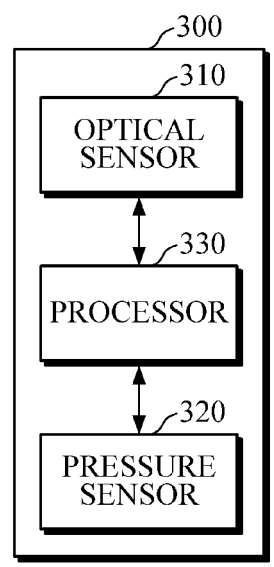
FIG. 3 is a block diagram illustrating an example of an antioxidant sensor according to an example embodiment.

FIG. 3 is a block diagram illustrating an example of an antioxidant sensor according to an example embodiment.

The antioxidant sensor 300 of FIG. 3 is a device for non-invasively measuring an antioxidant value of an object, and may be embedded in a handle, a button, an electronic device, and the like. Further, the antioxidant sensor 300 of FIG. 3 may be enclosed in a housing to be provided as a separate device. In this case, examples of the electronic device may include a cellular phone, a smartphone, a tablet personal computer (PC), a laptop computer, a personal digital assistant (PDA), a portable multimedia player (PMP), a navigation device, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 3, the antioxidant sensor 300 includes an optical sensor 310, a pressure sensor 320, and a processor 330.

The optical sensor 310 may emit light of different wavelengths to an object, and may receive light reflected or scattered from the object.

For example, when the object comes into contact with the optical sensor 310, the optical sensor 310 may emit a second light having a second wavelength to the object, and may receive the second light reflected or scattered from the object. In this case, the second wavelength may be a green wavelength included in a wavelength band, in which a hemoglobin signal is measured, e.g., an absorption band of hemoglobin. In this case, contact of the object with the optical sensor 310 may be determined based on whether contact pressure between the object and the optical sensor 310 exceeds a set first threshold pressure, or may be determined based on a sensor value of a touch sensor which is separately provided.

In another example, if contact pressure between the object and the optical sensor 310 exceeds a set second threshold pressure, the optical sensor 310 may emit a first light having a first wavelength to the object and may receive the first light reflected or scattered from the object. In this case, the first wavelength may be a blue wavelength included in a wavelength band, in which an antioxidant signal is measured, e.g., an absorption band of an antioxidant.

In yet another example, when the object comes into contact with the optical sensor 310, the optical sensor 310 may emit a third light having a third wavelength to the object, and may receive the third light reflected or scattered from the object. In this case, the third wavelength may be a wavelength, at which a preprocessing signal for preprocessing a hemoglobin signal and/or an antioxidant signal may be measured. For example, the third wavelength may be a blue wavelength, a green wavelength, or a red wavelength, which is different from the first wavelength and the second wavelength.

The pressure sensor 320 may measure contact pressure between the object and the optical sensor 310. In one example embodiment, the pressure sensor 320 may measure a contact force between the object and the optical sensor 310, and may obtain contact pressure by dividing the measured contact force by a predetermined area. The predetermined area may be a value stored as a default value in the antioxidant sensor 300. In another example, the pressure sensor 320 may measure a contact force and a contact area between the object and the optical sensor 310, and may obtain contact pressure by dividing the measured contact force by the measured contact area.

The pressure sensor 320 may be disposed at a bottom portion, a top portion, a middle portion, a side portion, and the like of the optical sensor 310. However, the position of the pressure sensor 120 is not limited thereto, and the pressure sensor 120 may be disposed at any position with respect to the optical sensor 310 as long as the pressure sensor 120 may measure contact pressure between the object and the optical sensor 310.

In one example embodiment, the pressure sensor 120 may include a force sensor, an acceleration sensor, a piezoelectric film, a load cell, radar, a strain gauge, and the like.

The processor 330 may control the overall operation of the antioxidant sensor 300, and may include one or more processors, a memory, and a combination thereof.

The processor 330 may detect contact between the object and the optical sensor 310. In one example embodiment, the processor 330 may detect contact between the object and the optical sensor 310 based on the contact pressure measured by the pressure sensor 320. For example, if the measured contact pressure exceeds a set first threshold pressure, the processor 330 may determine that the object is in contact with the optical sensor 310. In another example, the antioxidant sensor 300 includes a touch sensor disposed on a top portion of the optical sensor 310, and the processor 330 may detect contact between the object and the optical sensor 310 based on a sensor value of the touch sensor.

The processor 330 may determine a contact portion of the object in contact with the optical sensor 310. In this case, the contact portion may include a finger, a palm, a wrist, and the like.

In one example embodiment, the processor 330 may inquire a user about a contact portion of the object in contact with the optical sensor 310, and may determine the contact portion of the object based on a response to the inquiry from the user. For example, before or after the object comes into contact with the optical sensor 310, the processor 330 may inquire a user about a contact portion between the object and the optical sensor 310. However, the time of inquiring about the contact portion is not limited thereto, and the processor 330 may inquire about the contact portion between the object and the optical sensor 310 at any time without specific limitation.

In another example, the processor 330 may determine a hemoglobin index, and may determine a contact portion of the object in contact with the optical sensor 310 based on the determined hemoglobin index.

More specifically, once the object is in contact with the optical sensor 310, the processor 330 may control the optical sensor 310 to emit the second light of the second wavelength to the object, may receive the second light reflected or scattered from the object, and may obtain a hemoglobin signal based on the received second light. Further, the processor 330 may control the optical sensor 310 to emit the third light of the third wavelength to the object, may receive the third light reflected or scattered from the object, and may obtain a preprocessing signal based on the received third light. In addition, the processor 330 may obtain a hemoglobin index by normalizing the obtained hemoglobin signal. For example, the processor 330 may normalize the hemoglobin signal by subtracting the preprocessing signal from the hemoglobin signal or by dividing the hemoglobin signal by the preprocessing signal, and may obtain the normalized hemoglobin signal as the hemoglobin index.

The processor 330 may determine an interval (or a range), in which a value of the obtained hemoglobin index is included, and may determine a contact portion of the object in contact with the optical sensor 310 based on the determined interval. For example, if the obtained hemoglobin index is included in a first interval, the processor 330 may determine that the contact portion is a finger; if the obtained hemoglobin index is included in a second interval, the processor 330 may determine that the contact portion is a palm; and if the obtained hemoglobin index is included in a third interval, the processor 330 may determine that the contact portion is a wrist. In this case, the interval, in which the hemoglobin index is included, and the contact portion corresponding to the hemoglobin index may be pre-generated in the form of a matching table, and may be stored in an internal and/or external memory of the processor 330.

Upon determining the contact portion of the object in contact with the optical sensor 310, the processor 330 may set a second threshold pressure for measuring an antioxidant signal according to the determined contact portion. In this case, the processor 330 may set, as the second threshold pressure, different pressure values according to contact portions. For example, if a contact portion of the object in contact with the optical sensor 310 is a finger, the processor 330 may set a first pressure as the second threshold pressure. Further, if a contact portion of the object in contact with the optical sensor 310 is a palm, the processor 330 may set a second pressure as the second threshold pressure. In addition, if a contact portion of the object in contact with the optical sensor 310 is a wrist, the processor 330 may set a third pressure as the second threshold pressure. The first, second, and the third pressures may be preset and stored in advance in the internal and/or external memory of the processor 330. The first through the third pressures may have values different from each other.

Upon setting the second threshold pressure, the processor 330 may perform operation to guide a user's action so that contact pressure between the object and the optical sensor 310 may exceed the set second threshold pressure.

In one example embodiment, the processor 330 may compare the measured contact pressure with the second threshold pressure; and if the measured contact pressure is less than or equal to the second threshold pressure, the processor 330 may adjust at least one of a quantity of light or a flickering speed of one or more light sources of the optical sensor 310, to induce an increase in contact pressure between the object and the optical sensor 310.

In another example, the processor 330 may compare the measured contact pressure with the second threshold pressure; and if the measured contact pressure is less than or equal to the second threshold pressure, the processor 330 may generate a user's action guide information for increasing contact pressure between the object and the optical sensor 310 (e.g., information indicating that the contact pressure between the object and the optical sensor 310 is to be increased), and may provide the generated action guide information to the user through an output device. In this case, the output device may include a visual output device (e.g., display, etc.), an audio output device (e.g., speaker, etc.), and/or a tactile output device (e.g., vibrator, etc.).

If contact pressure between the object and the optical sensor 310 exceeds the second threshold pressure, the processor 330 may control the optical sensor 310 to emit the first light of the first wavelength to the object, may receive the first light reflected or scattered from the object, and may obtain an antioxidant signal based on the received first light. Further, the processor 330 may control the optical sensor 310 to emit the third light of the third wavelength to the object, may receive the third light reflected or scattered from the object, and may obtain a preprocessing signal based on the received third light.

The processor 330 may preprocess the obtained antioxidant signal by using the obtained preprocessing signal. For example, the processor 330 may normalize the antioxidant signal by subtracting the preprocessing signal from the antioxidant signal or by dividing the antioxidant signal by the preprocessing signal. In this manner, the processor 330 may eliminate an effect of a substance, other than an antioxidant substance, from the measured antioxidant signal.

The processor 330 may determine an antioxidant value by analyzing the preprocessed antioxidant signal. For example, the processor 330 may determine an antioxidant value of the object by using an antioxidant value estimation model. Here, the antioxidant value estimation model defines a relationship between an antioxidant signal and an antioxidant value, and may be pre-generated by regression analysis or machine learning and may be stored in an internal and/or external memory of the processor 330. The antioxidant value estimation model may be built in the form of a mathematical algorithm and/or a matching table, but is not limited thereto.

The processor 330 may provide the determined antioxidant value to a user through an output device. Further, if the antioxidant value is lower than or equal to a predetermined threshold value, the processor 330 may generate information on recommendation to increase the antioxidant value and may provide the information to the user through the output device. For example, if an antioxidant value is lower than or equal to a predetermined threshold level, the processor 330 may generate recommendation information, such as "eat more vegetables," "cut down on smoking," "cut down on alcohol consumption," "exercise more," "reduce stress," and the like, and may provide the recommendation information to the user through the output device.

The processor 330 may include at least one hardware among a central processing unit (CPU), a microprocessor, a graphic processing unit (GPU), application specific integrated circuits (ASICs), digital signal processors (DSPs), digital signal processing devices (DSPDs), programmable logic devices (PLDs), or field programmable gate arrays (FPGAs), without being limited thereto.

Figure 4:
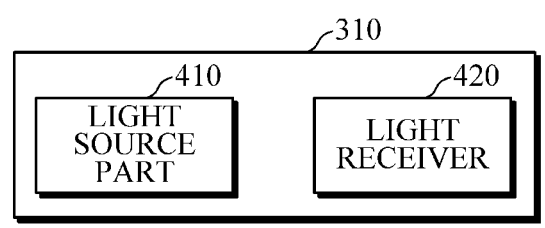
FIG. 4 is a block diagram illustrating an example of an optical sensor according to an example embodiment.

FIG. 4 is a block diagram illustrating an example of an optical sensor according to an example embodiment.

Referring to FIG. 4, the optical sensor 310 includes a light source part 410 and a light receiver 420.

The light source part 410 includes a plurality of light sources, including a first light source for emitting a first light of a first wavelength to an object, a second light source for emitting a second light of a second wavelength to the object, and a third light source for emitting a third light of a third wavelength to the object.

Each of the plurality of light sources may emit light of the same wavelength or light of different wavelengths, and wavelengths of light emitted by each of the plurality of light sources may vary according to the purpose of measurement or types of an analyte. Further, each of the plurality of light sources is not necessarily a single light-emitting body, and may be formed of an array of a plurality of light-emitting bodies. In the case where each of the light sources is formed of a plurality of light-emitting bodies, the plurality of light-emitting bodies may emit light of the same wavelength or light of different wavelengths. In addition, the plurality of light-emitting bodies may be classified into a plurality of groups, and each group of the light-emitting bodies may emit light of different wavelengths. In one example embodiment, each light source may be formed as a light emitting diode (LED), a laser diode, a phosphor, and the like.

Each light source may be driven sequentially or simultaneously under the control of the processor. In this case, light source driving conditions, such as an emission time, a driving sequence, a current intensity, a pulse duration, and the like of each light source may be preset.

In one example embodiment, the light source part 410 may further include at least one optical element (e.g., a reflecting mirror, a filter, etc.) for directing light emitted by each of the light sources toward a desired position of an object or for selecting light of a desired wavelength from among light beams emitted by each of the light sources.

The light receiver 420 may receive light reflected or scattered from the object. In one example embodiment, the light receiver 420 may be implemented as a photodetector or a spectrometer. Here, the photodetector may receive light reflected or scattered from an object, and may convert the received light into an electric signal. Examples of the photodetector may include a photo diode, a photo transistor (PTr), an image sensor (Charge-Coupled Device (CCD), Complementary Metal Oxide Semiconductor (CMOS), etc.) and the like. Further, the spectrometer may receive light reflected or scattered from an object and may separate the received light, and may include an interference spectrometer, a grating spectrometer, a prism spectrometer, and the like.

In one example embodiment, the light receiver 420 may further include at least one optical element (e.g., a reflecting mirror, a filter, etc.) for directing light reflected or scattered from the object toward the light receiver 420 or for selecting light of a desired wavelength from among light beams reflected or scattered from the object.

Figure 5:
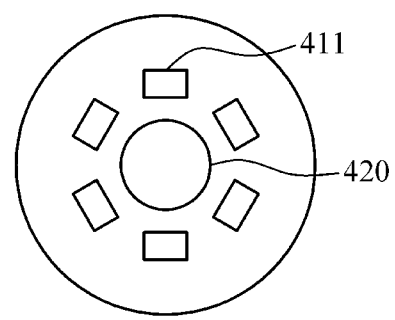
FIG. 5 is a diagram illustrating an example of arrangement of a light source part and a light receiver according to an example embodiment.
Figure 6:
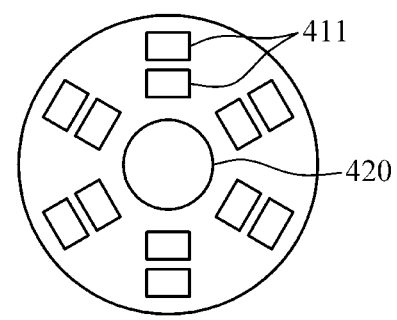
FIG. 6 is a diagram illustrating an example of arrangement of a light source part and a light receiver according to an example embodiment.

FIGS. 5 and 6 are diagrams illustrating examples of arrangement of a light source part and a light receiver according to example embodiments.

Referring to FIGS. 5 and 6, each light source 411 of the light source part may be disposed around the light receiver 420 to enclose the light receiver 420. In this case, each light source 411 may be disposed around the light receiver 420 to enclose the light receiver 420 in a single layer (FIG. 5) or in two layers (FIG. 6). However, the light source 411 is not limited thereto, and may be disposed to enclose the light receiver 420 in three or more layers.

Figure 7:
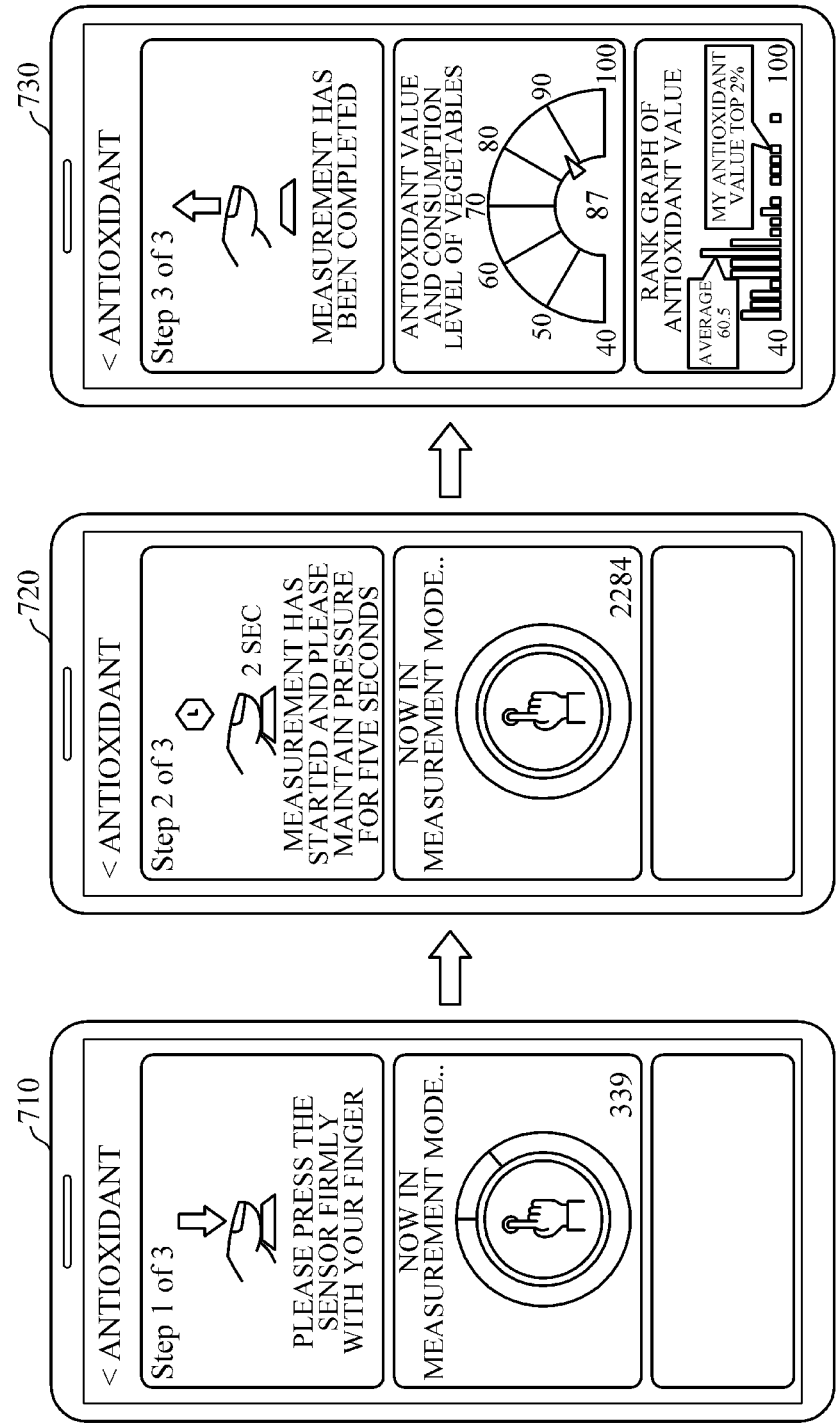
FIG. 7 is a diagram illustrating an example of outputting a user's action guide information for increasing contact pressure between an object and an optical sensor, and an antioxidant value measurement result according to an example embodiment.

FIG. 7 is a diagram illustrating an example of outputting a user's action guide information for increasing contact pressure between an object and an optical sensor, and an antioxidant value measurement result according to an example embodiment.

Referring to FIG. 7, as shown in 710, when a subject comes into contact with an optical sensor, a message "please press the sensor firmly with your finger" is displayed in an upper portion of a display along with an image showing a finger pressing a sensor. In one embodiment, a current contact pressure and a second threshold pressure may be displayed in a lower portion of the display. For example, a current contact pressure '339' may be displayed in the lower portion of the display, as shown in FIG. 710.

If the measured contact pressure exceeds the second threshold pressure, a message "measurement has started and please maintain pressure for five seconds" may be displayed along with an image showing a finger remaining in place while pressing the sensor, as shown in 720. Also, a current contact pressure '2284' may be displayed in the lower portion of the display, as shown in FIG. 720.

Upon completing measurement of an antioxidant value, a message "measurement has been completed" may be displayed in the upper portion of the display along with an image showing an action of lifting a finger from the sensor; a graph showing an antioxidant value and a consumption level of vegetables may be displayed in a middle portion of the display; and a graph showing a rank of a user's antioxidant value relative to a plurality of other users may be displayed in the lower portion of the display, as shown in 730.

Figure 8:
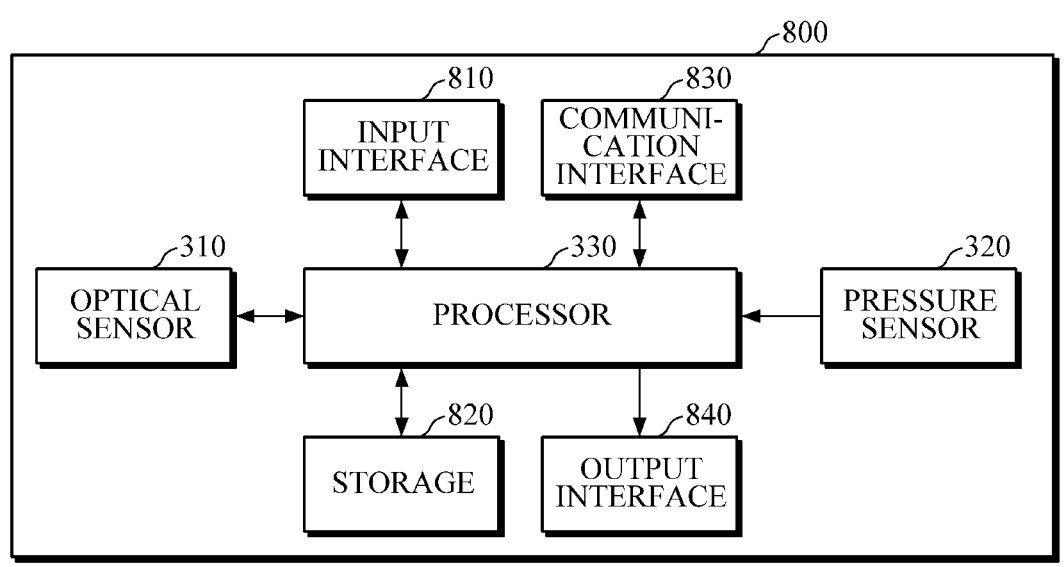
FIG. 8 is a block diagram illustrating an example of an antioxidant sensor according to an example embodiment.

FIG. 8 is a block diagram illustrating another example of an antioxidant sensor according to an example embodiment.

The antioxidant sensor 800 of FIG. 8 is a device for non-invasively measuring an antioxidant value of an object, and may be embedded in a handle, a button, an electronic device, and the like. Further, the antioxidant sensor 800 of FIG. 8 may be enclosed in a housing to be provided as a separate device. In this case, examples of the electronic device may include a cellular phone, a smartphone, a tablet PC, a laptop computer, a personal digital assistant (PDA), a portable multimedia player (PMP), a navigation device, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 8, the antioxidant sensor 800 includes the optical sensor 310, the pressure sensor 320, the processor 330, an input interface 810, a storage 820, a communication interface 830, and an output interface 840. Here, the optical sensor 310, the pressure sensor 320, and the processor 330 are described above with reference to FIG. 3, such that detailed description thereof will be omitted.

The input interface 810 may receive an input of various operation signals from a user. In one example embodiment, the input interface 810 may include a keypad, a dome switch, a touch pad (e.g., static pressure and/or capacitance type), a jog wheel, a jog switch, a hardware (H/W) button, and the like. Particularly, the touch pad, which forms a layer structure with a display, may be called a touch screen.

The storage 820 may store programs or commands for operation of the antioxidant sensor 800, and may store data input to and output from the antioxidant sensor 800. Further, the storage 820 may store data processed by the antioxidant sensor 800, data (e.g., antioxidant value estimation model) used for data processing of the antioxidant sensor 800, and the like.

The storage 820 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the antioxidant sensor 800 may operate an external storage medium, such as web storage and the like, which performs a storage function of the storage 820 on the Internet.

The communication interface 830 may communicate with an external device. For example, the communication interface 830 may transmit, to the external device, data used by the antioxidant sensor 800, processing result data of the antioxidant sensor 800, and the like; or may receive, from the external device, various data relevant or useful for measuring an antioxidant signal and/or determining an antioxidant value.

In this case, the external device may be medical equipment using the data used by the antioxidant sensor 800 or the processing result data of the antioxidant sensor 800, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation device, an MP3 player, a digital camera, a wearable device, and the like, but the external device is not limited thereto.

The communication interface 830 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely given as examples and is not intended to be limiting.

The output interface 840 may output the data used by the antioxidant sensor 800, the processing result data of the antioxidant sensor 800, and the like. In one example embodiment, the output interface 840 may output the data used by the antioxidant sensor 800, the processing result data of the antioxidant sensor 800, and the like by using at least one of an acoustic method, a visual method, and/or a tactile method. To this end, the output interface 840 may include a display, a speaker, a vibrator, and the like.

Figure 9:
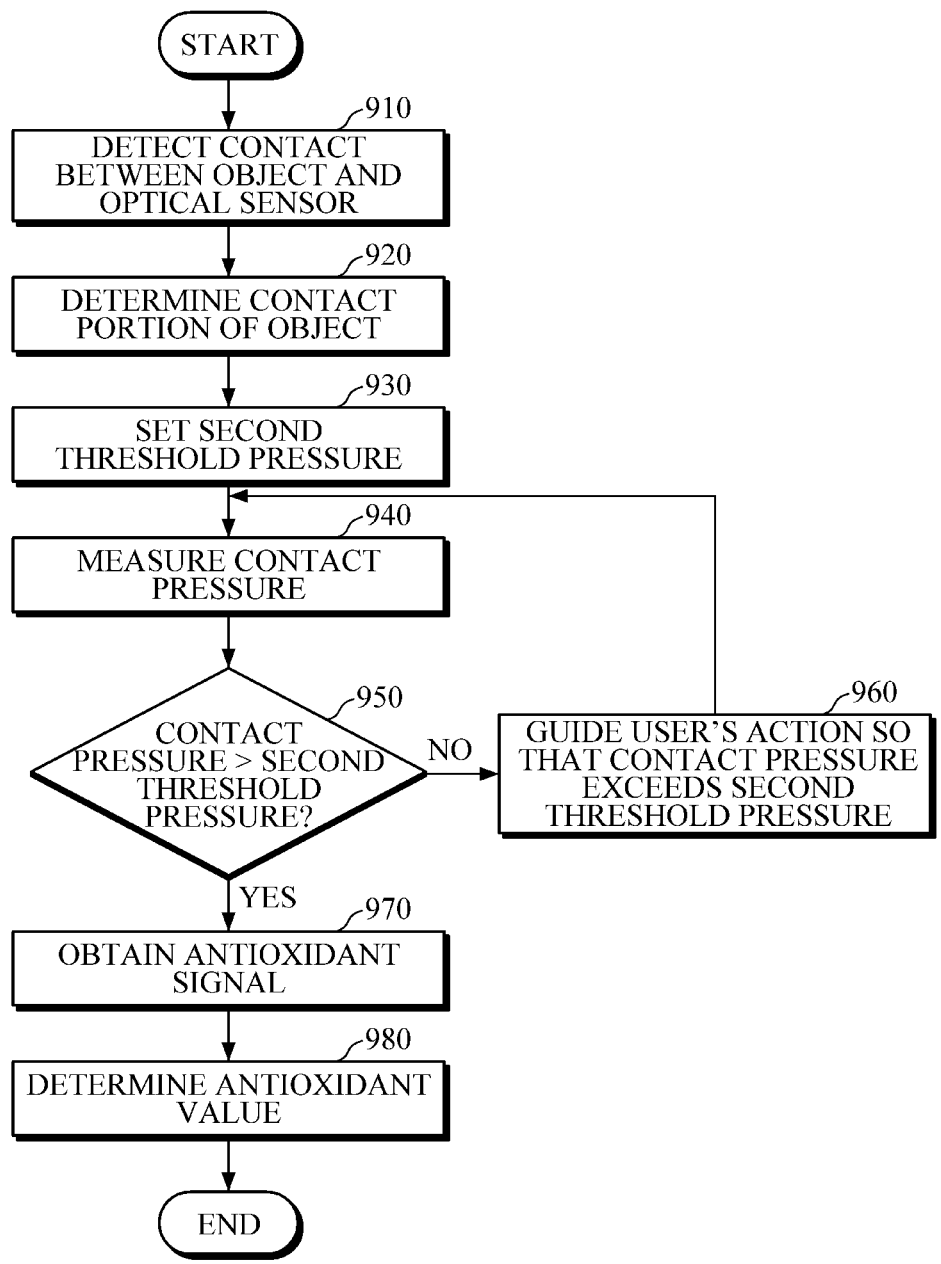
FIG. 9 is a flowchart illustrating an example of a method of measuring an antioxidant value according to an example embodiment.

FIG. 9 is a flowchart illustrating an example of a method of measuring an antioxidant value according to an example embodiment. The method of measuring an antioxidant value of FIG. 9 may be performed by any one of the antioxidant sensor 300 of FIG. 3 or the antioxidant sensor 800 of FIG. 8.

Referring to FIG. 9, the antioxidant sensor may detect contact between an object and an optical sensor in 910. In one example embodiment, the antioxidant sensor may detect contact between the object and the optical sensor based on contact pressure measured by a pressure sensor. For example, if the measured contact pressure exceeds a set first threshold pressure, the antioxidant sensor may determine that the object is in contact with the optical sensor. In another example, the antioxidant sensor may detect the contact between the object and the optical sensor based on a sensor value of a touch sensor provided at the top of the optical sensor.

The antioxidant sensor may determine a contact portion of the object in contact with the optical sensor in 920. In this case, the contact portion may include a finger, a palm, a wrist, and the like.

Upon determining the contact portion of the object in contact with the optical sensor, the antioxidant sensor may set a second threshold pressure for measuring an antioxidant signal based on the determined contact portion in 930. For example, if a contact portion of the object in contact with the optical sensor is a finger, the antioxidant sensor may set a first pressure as the second threshold pressure. Further, if a contact portion of the object in contact with the optical sensor 310 is a palm, the antioxidant sensor may set a second pressure as the second threshold pressure. In addition, if a contact portion of the object in contact with the optical sensor 310 is a wrist, the antioxidant sensor may set a third pressure as the second threshold pressure. The first, the second, and the third pressures may be preset and stored in advance in the antioxidant sensor (e.g., memory of the processor in the antioxidant sensor). The first through the third pressures may have values different from each other.

Upon setting the second threshold pressure, the antioxidant sensor may measure contact pressure between the object and the optical sensor in 940. In one example embodiment, the antioxidant sensor may measure a contact force between the object and the optical sensor, and may obtain contact pressure by dividing the measured contact force by a predetermined area. In another example, the antioxidant sensor may measure a contact force and a contact area between the object and the optical sensor, and may obtain contact pressure by dividing the measured contact force by the measured contact area.

The antioxidant sensor may compare the measured contact pressure with the second threshold pressure in 950. If the measured contact pressure is less than or equal to the second threshold pressure, the antioxidant sensor may perform operation to guide a user's action in 960 so that contact pressure between the object and the optical sensor may exceed the set second threshold pressure. For example, the antioxidant sensor may compare the measured contact pressure with the second threshold pressure: and if the measured contact pressure is less than or equal to the second threshold pressure, the antioxidant sensor may adjust at least one of a quantity of light or a flickering speed of one or more light sources of the optical sensor, to induce an increase in contact pressure between the object and the optical sensor. In another example, the antioxidant sensor may compare the measured contact pressure with the second threshold pressure; and if the measured contact pressure is less than or equal to the second threshold pressure, the antioxidant sensor may generate a user's action guide information for increasing contact pressure between the object and the optical sensor (e.g., information indicating that the contact pressure between the object and the optical sensor is to be increased), and may provide the generated action guide information to the user through an output device. In this case, the output device may include a visual output device (e.g., display, etc.), an audio output device (e.g., speaker, etc.), and/or a tactile output device (e.g., vibrator, etc.).

If the measured contact pressure exceeds the set second threshold pressure, the antioxidant sensor may control the optical sensor to emit a first light of a first wavelength to the object, may receive the first light reflected or scattered from the object, and may obtain an antioxidant signal based on the received first light in 970.

The antioxidant sensor may determine an antioxidant value of the object by analyzing the obtained antioxidant signal in 980. For example, the antioxidant sensor may determine an antioxidant value of the object by using an antioxidant value estimation model. Here, the antioxidant value estimation model defines a relationship between an antioxidant signal and an antioxidant value, and may be pre-generated by regression analysis or machine learning and stored in an internal and/or external memory of the antioxidant sensor. The antioxidant value estimation model may be built in the form of a mathematical algorithm and/or a matching table, but is not limited thereto.

In addition, in one example embodiment, upon obtaining the antioxidant signal, the antioxidant sensor may preprocess the obtained antioxidant signal. For example, upon obtaining the antioxidant signal, the antioxidant sensor may control the optical sensor to emit a third light of a third wavelength to the object, may receive the third light reflected or scattered from the object, and may obtain a preprocessing signal based on the received third light. Further, the antioxidant sensor may preprocess the obtained antioxidant signal by normalizing the antioxidant signal by subtracting the preprocessing signal from the antioxidant signal or by dividing the antioxidant signal by the preprocessing signal.

Furthermore, in one example embodiment, upon determining the antioxidant value, the antioxidant sensor may provide the determined antioxidant value to a user through an output device. If the antioxidant value is lower than or equal to a predetermined threshold value, the antioxidant sensor may generate recommendation information to increase the antioxidant value and may provide the recommendation information to the user through the output device. For example, if an antioxidant value is lower than or equal to a predetermined threshold level, the antioxidant sensor may generate recommendation, such as "eat more vegetables," "cut down on smoking," "cut down on alcohol consumption," "exercise more," "reduce stress," and the like, and may provide the recommendation information to the user through the output device.

Figure 10:
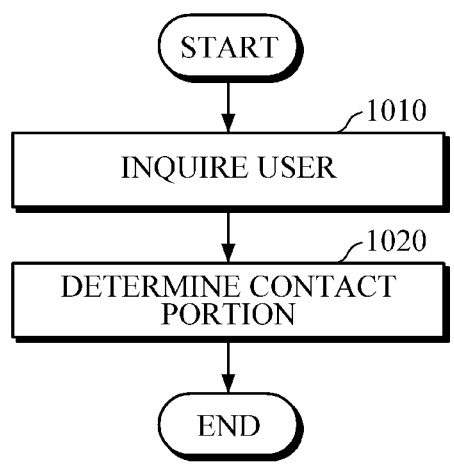
FIG. 10 is a flowchart illustrating an example of a method of determining a contact portion of an object in contact with an optical sensor according to an example embodiment.

FIG. 10 is a flowchart illustrating an example of a method of determining a contact portion of an object in contact with an optical sensor according to an example embodiment. The method of FIG. 10 may be an example of determining of the contact portion in 920 of FIG. 9.

Referring to FIG. 10, the antioxidant sensor may inquire a user about a contact portion of the object in contact with the optical sensor in 1010. For example, before or after the object comes into contact with the optical sensor, the antioxidant sensor may inquire a user about a contact portion between the object and the optical sensor. However, the time of inquiring about the contact portion is not limited thereto, and the antioxidant sensor may inquire about the contact portion of the object in contact with the optical sensor at any time without specific limitation.

The antioxidant sensor may determine the contact portion of the object based on a response to the inquiry from the user in 1020.

Figure 11:
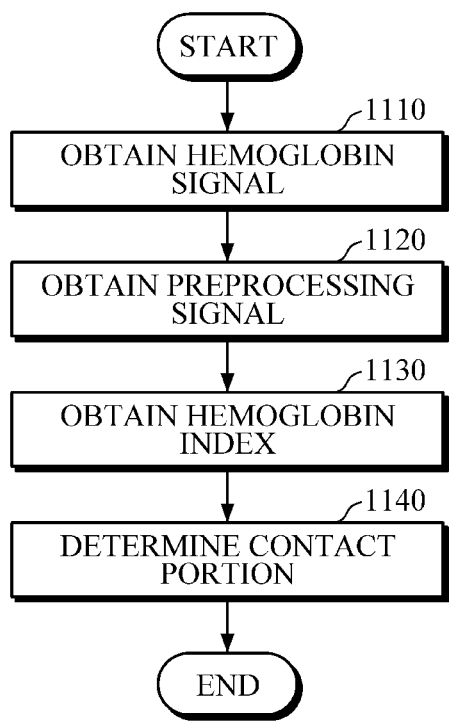
FIG. 11 is a flowchart illustrating an example of a method of determining a contact portion of an object in contact with an optical sensor according to an example embodiment.

FIG. 11 is a flowchart illustrating another example of a method of determining a contact portion of an object in contact with an optical sensor according to an example embodiment. The method of FIG. 11 may be an example of determining of the contact portion in 920 of FIG. 9.

Referring to FIG. 11, the antioxidant sensor may control the optical sensor to emit a second light of a second wavelength to the object, may receive the second light reflected or scattered from the object, and may obtain a hemoglobin signal based on the received second light in 1110.

The antioxidant sensor may control the optical sensor to emit a third light of a third wavelength to the object, may receive the third light reflected or scattered from the object, and may obtain a preprocessing signal based on the received third light in 1120.

The antioxidant sensor may obtain a hemoglobin index by normalizing the obtained hemoglobin signal based on the obtained preprocessing signal in 1130. For example, the antioxidant sensor may normalize the hemoglobin signal by subtracting the preprocessing signal from the hemoglobin signal or by dividing the hemoglobin signal by the preprocessing signal, and may obtain the normalized hemoglobin signal as the hemoglobin index.

The antioxidant sensor may determine an interval (or a range), in which a value of the obtained hemoglobin index is included, and may determine a contact portion of the object in contact with the optical sensor based on the determined interval in 1140. For example, if the obtained hemoglobin index is included in a first interval, the antioxidant sensor may determine that the contact portion is a finger; if the obtained hemoglobin index is included in a second interval, the antioxidant sensor may determine that the contact portion is a palm; and if the obtained hemoglobin index is included in a third interval, the antioxidant sensor may determine that the contact portion is a wrist. In this case, the interval, in which the hemoglobin index is included, and the contact portion corresponding to the hemoglobin index may be pre-generated in the form of a matching table, and may be stored in an internal and/or external memory of the antioxidant sensor.

Embodiments of the disclosure may be implemented as a computer-readable code stored in a computer-readable recording medium. Codes and code segments for implementing the disclosure may be easily deduced by one of ordinary skill in the art. The computer-readable recording medium may be any type of recording medium in which data is stored in a computer-readable manner. Examples of the computer-readable recording medium include a ROM, a RAM, a CD-ROM, a magnetic tape, a floppy disc, an optical disk, and the like. Further, the computer-readable recording medium may be distributed over a plurality of computer systems connected to a network so that a computer-readable recording medium is written thereto and executed therefrom in a decentralized manner.

The disclosure has been described herein with regard to example embodiments. However, it will be obvious to those skilled in the art that various modifications may be made without departing from the gist of the disclosure. Therefore, it is to be understood that that the scope of the disclosure is not limited to the above-mentioned embodiments, but is intended to include various modifications and equivalents included within the spirit and scope of the appended claims.

What is claimed is:

1. An antioxidant sensor comprising:
   a pressure sensor configured to obtain a contact pressure between an object and an optical sensor;
   a processor configured to:
   set a first threshold pressure and a plurality of second threshold pressures;
   determine whether the object is in contact with the optical sensor based on the obtained contact pressure exceeding the first threshold pressure, and determine a contact portion of the object in contact with the optical sensor; and
   select a second threshold pressure, among the plurality of second threshold pressures, according to the determined contact portion, wherein the plurality of second threshold pressures respectively correspond to different contact portions, and the optical sensor configured to, based on the obtained contact pressure exceeding a set the selected second threshold pressure, emit a first light of a first wavelength to the object, and to receive the first light reflected or scattered from the object, wherein the processor is configured to determine an antioxidant value based on the received first light.

2. The antioxidant sensor of claim 1, wherein the processor is further configured to control operation to guide a user such that the contact pressure between the object and the optical sensor exceeds the set first threshold pressure.

3. The antioxidant sensor of claim 2, wherein the processor is further configured to, based on the obtained contact pressure being less than or equal to the set first threshold pressure, adjust at least one of a quantity of light and a flickering speed of the optical sensor.

4. The antioxidant sensor of claim 2, wherein the processor is further configured to, based on the obtained contact pressure being less than or equal to the set first threshold pressure, output information indicating that the contact pressure between the object and the optical sensor is to be increased.

5. The antioxidant sensor of claim 1, wherein the first wavelength is included in an absorption band of an antioxidant substance.

6. The antioxidant sensor of claim 5, wherein the first wavelength is a blue wavelength.

7. The antioxidant sensor of claim 1, wherein the processor is further configured to control to inquire a user about the contact portion of the object and determine the contact portion of the object based on a response from the user.

8. The antioxidant sensor of claim 1, wherein the optical sensor is further configured to emit a second light of a second wavelength and a third light of a third wavelength to the object, and receive the second light and the third light reflected or scattered from the object; and the processor is further configured to obtain a hemoglobin index based on the received second light and the received third light, and determine the contact portion of the object based on the obtained hemoglobin index.

9. The antioxidant sensor of claim 8, wherein the second wavelength is included in an absorption band of hemoglobin; and the third wavelength is different from the second wavelength.

10. The antioxidant sensor of claim 9, wherein the second wavelength is a green wavelength; and the third wavelength is a blue wavelength, the green wavelength, or a red wavelength.

11. The antioxidant sensor of claim 8, wherein the processor is further configured to obtain a hemoglobin signal based on the received second light, obtain a preprocessing signal based on the received third light, normalize the obtained hemoglobin signal by using the preprocessing signal, and obtain the normalized hemoglobin signal as the hemoglobin index.

12. The antioxidant sensor of claim 8, wherein the processor is further configured to determine the contact portion of the object based on a value of the hemoglobin index.

13. A method of obtaining an antioxidant value, the method comprising:

obtaining a contact pressure between an object and an optical sensor;

setting a first threshold pressure and a plurality of second threshold pressures;

based on the obtained contact pressure exceeding the first threshold pressure, determining that the object is in contact with the optical sensor and determining a contact portion of the object in contact with the optical sensor;

selecting a second threshold pressure, among the plurality of second threshold pressures, according to the determined contact portion, wherein the plurality of second threshold pressures respectively correspond to different contact portions;

based on the obtained contact pressure exceeding the selected second threshold pressure, emitting a first light of a first wavelength to the object, and receiving the first light reflected or scattered from the object; and determining an antioxidant value based on the received first light.

14. The method of claim 13, further comprising controlling to guide a user such that the contact pressure between the object and the optical sensor exceeds the set first threshold pressure.

15. The method of claim 14, wherein the controlling comprises, based on the obtained contact pressure being less than or equal to the set first threshold pressure, adjusting at least one of a quantity of light and a flickering speed of the optical sensor.

16. The method of claim 14, wherein the controlling comprises, based on the obtained contact pressure being less than or equal to the set first threshold pressure, outputting information indicating that the contact pressure between the object and the optical sensor is to be increased.

17. The method of claim 13, wherein the first wavelength is a blue wavelength included in an absorption band of an antioxidant substance.

18. The method of claim 13, wherein the determining the contact portion comprises:

inquiring a user about the contact portion of the object; and determining the contact portion of the object based on a response from the user.

19. The method of claim 13, wherein the determining the contact portion comprises:

emitting a second light of a second wavelength and a third light of a third wavelength to the object;

receiving the second light and the third light reflected or scattered from the object;

obtaining a hemoglobin index based on the received second light and the received third light; and determining the contact portion of the object based on the obtained hemoglobin index.

20. The method of claim 19, wherein the second wavelength is a green wavelength included in an absorption band of hemoglobin; and the third wavelength is a blue wavelength, the green wavelength, or a red wavelength which is different from the second wavelength.

21. The method of claim 19, wherein the obtaining the hemoglobin index comprises:

obtaining a hemoglobin signal based on the received second light;

obtaining a preprocessing signal based on the received third light;

normalizing the obtained hemoglobin signal by using the preprocessing signal; and obtaining the normalized hemoglobin signal as the hemoglobin index.

22. The method of claim 19, wherein the determining the contact portion comprises determining the contact portion of the object based on a value of the hemoglobin index.

* * * * *